United States Patent [19]

Aida et al.

[11] Patent Number: 4,960,107

[45] Date of Patent: Oct. 2, 1990

[54] ULTRASONIC MEDICAL TREATMENT APPARATUS

[75] Inventors: Satoshi Aida, Kanagawa; Nobuyuki Iwama, Tokyo; Syuzi Suzuki; Akihiro Ishiguro, both of Kanagawa, all of Japan

[73] Assignee: Kabushiki Kaisha Toshiba, Kawasaki, Japan

[21] Appl. No.: 251,839

[22] Filed: Sep. 30, 1988

[30] Foreign Application Priority Data

Sep. 30, 1987 [JP] Japan ................................ 62-249035
Apr. 26, 1988 [JP] Japan ................................ 63-101310

[51] Int. Cl.[5] ................................................ A61B 17/22
[52] U.S. Cl. .................................... 128/24 A; 606/128
[58] Field of Search ................ 128/24 A, 328, 660.03; 433/86; 606/128

[56] References Cited

U.S. PATENT DOCUMENTS

| | | | |
|---|---|---|---|
| 4,062,237 | 12/1977 | Fox | 128/661.01 X |
| 4,207,772 | 6/1980 | Stoller | 128/661.01 X |
| 4,470,305 | 9/1984 | O'Donnell | 128/661.01 X |
| 4,586,512 | 5/1986 | Do-huu et al. | 128/660.03 |
| 4,617,931 | 11/1984 | Dory | 128/328 |
| 4,622,972 | 11/1986 | Giebeler, Jr. | 128/24 A X |
| 4,646,756 | 3/1987 | Watmough et al. | 128/24 A X |

OTHER PUBLICATIONS

Sector–Vortex Phased Array Applicator for Ultrasound Focal Hyperthermia Progress in Hyperthermic Oncology; S. Umemura et al.; 1986.

Transducers for Producing Ultrasonic Waves; Journal of the Acoustical Society of America; vol. 25 No. 2; Oskar Mattiat; Mar. 1953.

*Primary Examiner*—Francis Jaworski
*Attorney, Agent, or Firm*—Oblon, Spivak, McClelland, Maier & Neustadt

[57] ABSTRACT

An ultrasonic medical treatment apparatus having an piezoelectric element for generating ultrasonic energy is provided. The element is constituted by a plurality of unit piezoelectric elements of two or more different shapes. The surface areas of these unit elements are substantially equal to each other. These unit elements can be individually removed as required.

11 Claims, 4 Drawing Sheets

ULTRASONIC MEDICAL TREATMENT APPARATUS

BACKGROUND OF THE INVENTION

1. Field of the Invention:

This invention relates to an ultrasonic medical treatment apparatus for use in giving medical treatment to a human body with ultrasonic energy, and more particularly to an applicator for use in such treatment.

2. Description of the Prior Art:

A shock wave type apparatus for destroying calculus (kidney stones) has received practical application. The apparatus utilizes shock wave energy generated by an electric discharge or by explosion. However, in recent years, the use of focused ultrasonic energy to destroy calculuses in a human body has become feasible. This method has become of major interest as a substitute for the utilization of shock wave energy. This is because the use of ultrasonic energy can result in a significant reduction in the size and the manufacturing cost of calculus-destroying apparatus. In addition, such apparatus requires substantially no expendable materials.

The conventional applicator for use in ultrasonic calculus-destroying apparatus has a spherical piezoelectric element that generates ultrasonic energy and concentrates the same on the focal point thereof.

The piezoelectric element type calculus-destroying apparatus usually generates acoustic energy smaller than that generated by an electric discharge shook wave type apparatus, when both have an applicator of the same area. Thus, in order to obtain the necessary acoustic energy, a piezoelectric element having a relatively larger area is required. However, such a piezoelectric element is usually made of ceramics. Thus, the size of a single concave piezoelectric element is inevitably limited. Therefore, a plurality of unit piezoelectric elements are combined so as to form the necessary area in combination.

FIGS. 4*a* through 4*c* show conventional applicators manufactured by the combination of unit piezoelectric elements. FIG. 4*a* shows an applicator formed by combination of plural circular concave piezoelectric elements 1*a* through 1*g*, which are all the same size. In this case, there are gaps between adjacent concave elements 1*a* through 1*g*. Thus, these gaps decrease the space factor of the applicator. FIG. 4*b* shows an applicator made by combination of plural hexagonal concave elements 2*a* through 2*g*. This applicator has a space factor higher than that of the applicator of FIG. 4*a*.

However, the outside diameter of this applicator is limited. Moreover, at the center of this applicator, a hole for inserting an imaging ultrasonic probe is often provided. Thus, the space factor of this applicator decreases at the periphery thereof. FIG. 4*c* shows an applicator provided with auxiliary small-size elements 3*a* through 3*f* that fill the periphery thereof. However, in general, the individual elements are respectively connected to plural separate driving circuits. Thus, when plural elements having different surface areas are used, the electrical loads of such driving circuits are varied in proportion to the respective surface areas. Thus, plural driving circuits with specifications different from each other are required. As a result, the apparatus becomes cumbersome and complicated. Moreover, this raises the manufacturing costs thereof.

FIG. 5 shows another conventional ultrasonic medical treatment applicator. In FIG. 5, an ultrasonic medical treatment applicator 4 has a base plate 5. The internal surface of base plate 5 is formed in a spherical configuration. As can be seen from the drawing, a plurality of unit elements 6 of equilateral hexagons are combined and adhere to the base plate 5 so as to constitute the applicator 4. The plural unit elements 6 are fixed such that ultrasonic energy generated from these elements 6 is accurately concentrated on a focal point. Thus, once the unit elements 6 are fixed accurately, the ultrasonic medical treatment applicator 4 functions steadily without being out of focus, and it is free from undesirable dispersion of the ultrasonic energy.

However, as described above, the unit elements 6 are made of ceramics. Thus, these elements 6 are susceptible to damage during the process of manufacturing the applicator 4 or its operation. Actually, it is not a rare case that even when the ultrasonic medical treatment applicator 4 is used, some of unit elements 6 are found to be defective. Such defectives of the unit elements 6 decrease the generation of ultrasonic energy. Moreover, the unit elements 6 are fixed to the base plate 5 so as to be united therewith. Thus, the entire ultrasonic medical treatment applicator 4, per se, must be replaced. Otberwise the maximum performance thereof cannot be completely insured.

As described above, in the conventional ultrasonic medical treatment applicator, there are problems as follows. When plural unit elements identical in size and shape are used, the space factor of the applicator decreases. When plural unit elements with surface areas different from each other are used in combination, the driving circuits therefor become complicated.

Moreover, in the conventional ultrasonic medical treatment applicator, plural unit elements are fixed to the base plate in order that the focuses of these elements invariably coincide with each other. However, this causes disadvantages in that when only a part of the unit elements become defective, the whole applicator must be replaced.

SUMMARY OF THE INVENTION

Accordingly, one object of the present invention is to provide an ultrasonic medical treatment apparatus with an applicator having a maximum space factor within the specified shape thereof.

Another object of the present invention is to provide an ultrasonic medical treatment apparatus with an applicator that can readily maintain the ultrasonic energy generated by an ultrasonic element at a maximum amount.

Briefly, in accordance with one aspect of this invention, there is provided an ultrasonic medical treatment apparatus having a piezoelectric element for generating ultrasonic energy. The element is constituted by a plurality of unit piezoelectric elements of two or more different shapes. The surface areas or sizes of these unit elements are substantially equal to each other.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
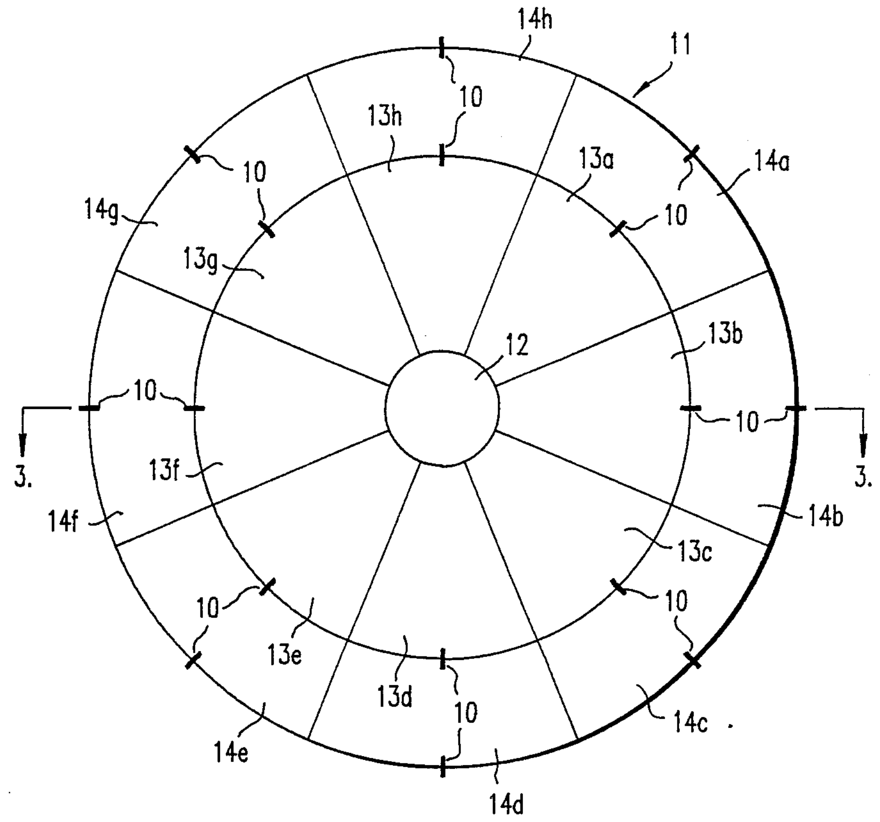
FIG. 1 is a plan view illustrating one embodiment according to the present invention.

Referring now to the drawings, wherein like reference numerals designate identical or corresponding parts throughout the several views, and more particularly to FIG. 1 thereof, one embodiment of this invention will be described.

In FIG. 1, a piezoelectric element 11 of an applicator (hereinafter, simply referred to as element) is formed in a circular concave shape of about 40 cm in diameter. At the center portion of the element 11, a hole 12 of about 8 cm in diameter is provided. This hole 12 is used for inserting an imaging ultrasonic probe (not shown).

The element 11 is constituted by sixteen unit piezoelectric elements (hereinafter, simply referred to as unit element) of two different shapes. Namely, eight unit elements 13*a* through 13*h* and eight unit elements 14*a* through 14*h* are provided. Specifically the shapes of the two kinds are formed such that the entire shape of element 11 is divided radially into eight portions. Further, the thus divided eight portions are each respectively divided into two portions in a concentric configuration with respect to the center hole 12. The eight portions inside the concentric circle are fan-shaped unit elements 13*a* through 13*h*. The eight portions outside the concentric circle are fan-shaped unit elements 14*a* through 14*h*. The diameter of the concentric circle is determined such that all the unit elements 13*a* through 13*h* and 14*a* through 14*h* are identical in area or size.

Here, the front electrodes of these unit elements 13*a* through 13*h* and 14*a* through 14*h* are connected in common to the ground potential. Thus, they can be connected without any electrical insulation.

Figure 2:
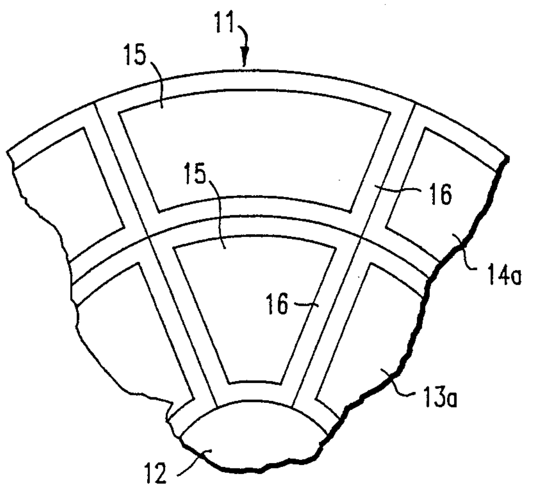
FIG. 2 is a partially enlarged back side view of the embodiment of FIG. 1.

However, the back electrodes 15 of these elements are separately connected to the respective driving circuits so as to receive signal voltages of 2 to 4 kV. When the individual unit elements are operated separately by the respective driving circuits, potential differences occur between the adjacent elements because of the signals being out of phase. To prevent a short circuit between these potential differences, portions 16 with no electrode are provided between the respective adjacent elements. The non-electrode portions 16 are about 1 mm or more in width as shown in FIG. 2. These unit elements are electrically insulated. However, they are constructed in close contact. Thus, the applicator in this embodiment can achieve stable construction.

This ultrasonic medical treatment applicator is constituted by a plurality of unit elements of shapes of two kinds as described above. The applicator has gaps of minimum size between the respective adjacent unit elements. Therefore, the space factor thereof can be enhanced. Moreover, these unit elements are identical in area. Thus, the driving circuits of identical specifications can be used. As a result, the entire apparatus can be simplified in configuration.

Moreover, according to the present invention, there is provided an ultrasonic medical treatment applicator having a spherical ultrasonic element constituted by a plurality of unit elements for generating ultrasonic energy, wherein the unit elements are detachably fixed to a base plate by the use of screws.

Figure 3:
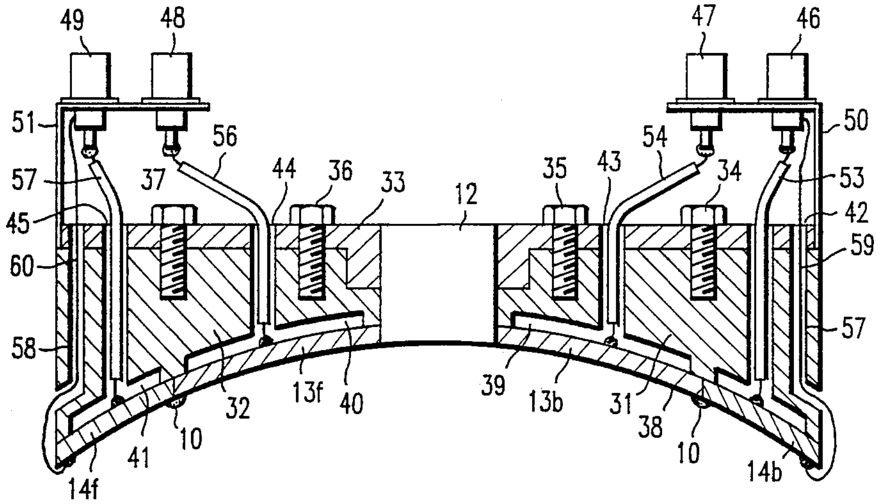
FIG. 3 is a cross-sectional view taken along line A—A of FIG. 1.
Figure 4A:
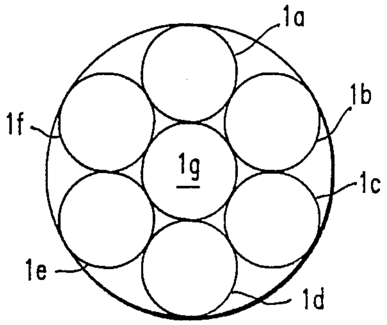
FIG. 4a PRIOR ART
FIGS. 4a through 4c are plan views of conventional examples.
Figure 4B:
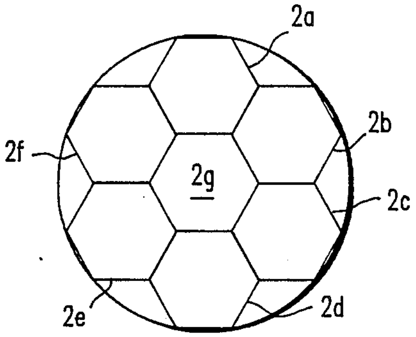
FIG. 4b PRIOR ART
Figure 4C:
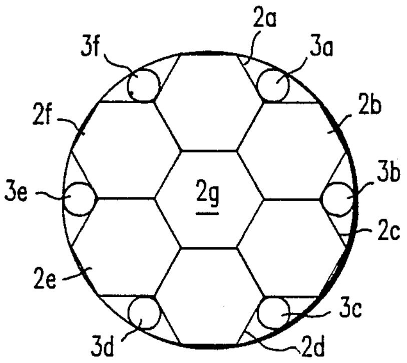
FIG. 4c PRIOR ART
Figure 5:
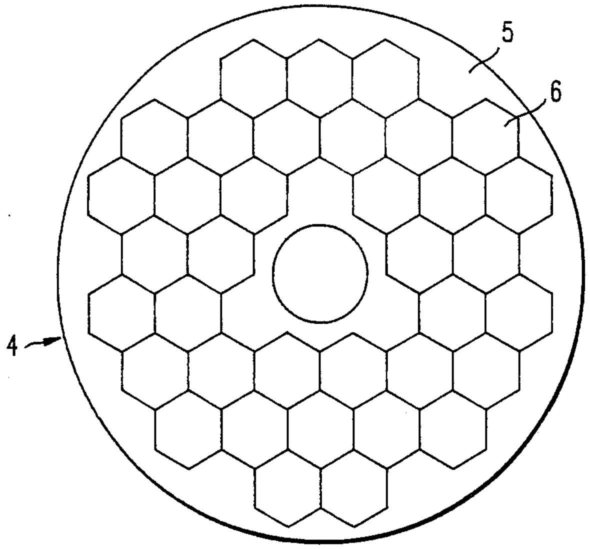
FIG. 5 PRIOR ART
FIG. 5 is a plan view illustrating another conventional example.

FIG. 3 is a cross-sectional view taken along line A—A of FIG. 1. In FIG. 3, the front surfaces of base plates 31 and 32 are partial portions of spherical face. A hole 12 is provided at the center of the spherical face. An imaging ultrasonic probe (not shown) is inserted into the hole 12. The base plates 31, 32, and other surrounding base plates (not shown, but eight pieces as a whole) respectively adhere to corresponding pairs of unit elements 13*a* and 14*a*, 13*b* and 14*b*, 13*c* and 14*c*, 13*d* and 14*d*, 13*e* and 14*e*, 13*f* and 14*f*, 13*g* and 14*g*, and 13*h* and 14*h* of FIG. 1. In FIG. 3, the base plates 31 and 32 are respectively secured by screws 34, 35, 36 and 37 to a supporting disk 33. Thus, these eight base plates 31, 32 and others can be independently removed from the supporting disk 33 by loosening the screws 34 through 37, as required. Gaps 38 through 41 are provided between the base plates 31 and 32 and the unit elements 13*b*, 14*b*, 13*f* and 14*f*, respectively.

Signal-lead passing bores 42 through 45 are provided piercing through the supporting disk 33 and the base plates 31 and 32, and reaching the gaps 38 through 41. Terminals 46 through 49 are provided at the periphery of the supporting disc 33 through L-shaped members 50 and 51. The signal electrodes 15 (shown in FIG. 2) provided on the back sides of the unit elements 13*b*, 14*b*, 13*f* and 14*f* are respectively connected to the terminals 46 through 49 by signal leads 53 through 66 by way of signal-lead passing bores 42 through 45. Ground-lead passing bores 57 and 58 are provided outside of the signal-lead passing bores 42 through 45. The unit elements 13*b*, 14*b*, 13*f* and 14*f* are connected by ground potential jumpers 10 on the front sides thereof. Further, the front sides of the unit elements 13*b*, 14*b*, 13*f* and 14*f* are connected to the outer portions of the terminals 46 through 49 by ground-leads 59 and 60 by way of the ground-lead passing bores 57 and 58.

The above-described construction has the following advantages. Namely, in the case where a unit element becomes defective and unable to perform necessary operations, the defective unit element can be readily removed by loosening screws so as to be repaired or replaced.

As described above, in this embodiment, the use of screws allows the unit elements to be removed. Thus, the repair or replacement of the unit elements can be readily performed. As a result, the ultrasonic medical treatment applicator in this embodiment can always maintain the ultrasonic energy at a required maximum amount. Moreover, the conventional unit elements are fixed to the base plate by use of an adhesive. The fixing process of the unit elements should be performed in a state where all the focuses of the unit elements accurately coincide with each other. This requires cumbersome and complicated procedures in manufacturing.

To the contrary, in this embodiment, first, the unit elements can be coarsely attached to the base plate by use of screws. Thereafter, the fine adjustment of focusing of the unit elements can be performed by use of screws. This can significantly reduce the above-mentioned cumbersome and complicated procedures in manufacturing. In addition, when adhesive is used instead of screws, the positions of unit elements are in danger of shifting while the adhesive is hardening. However, this problem can also be eliminated. The number of pairs of unit elements is not limited to eight, but a greater or smaller number of pairs may be used. However, the number of unit elements are determined taking into consideration such factors as the processing techniques of manufacturing materials, the probability of damage, and the cost necessary for repairs or replacement.

In the first and second embodiments, the unit elements are secured by screws to the base plate. However, instead of screwing, any other manner may be employed so long as the unit elements are readily detachable. For example, the unit elements and the base plate may be sandwiched by use of securing parts. Otherwise, they may be attracted to each other by use of magnetic force. Whatever construction is used, advantages equal to those of the present invention can be obtained so long as the fine adjustment of positions of unit elements can be performed.

In addition, the shape of the applicator is not limited to a circle. Also, the appearance of the unit elements is not limited to a fan-shape, a circle, or a polygon. Specifically, any unit elements of different appearances may be selectively utilized.

Moreover, according to the present invention, it is desirable that the areas of the unit elements be identical. However, the embodiment of the present invention can be practiced by use of unit elements having areas substantially identical.

Furthermore, in the previous description, the embodiment has been described as to an apparatus for destroying calculuses in a human body. However, the present invention may be applied to other apparatus such as an ultrasonic hyperthermia.

Obviously, numerous additional modifications and variations of the present invention are possible in light of the above teachings. It is therefore to be understood that within the scope of the appended claims, the invention may be practiced otherwise than as specifically described herein.

What is claimed is:

1. An ultrasonic medical treatment apparatus comprising:
- an ultrasonic generating element for generating ultrasonic energy for treatment of a patient, said element including a plurality of unit elements each unit element having one of two or more different shapes, and said unit elements having surface areas substantially equal to each other, wherein the total area occupied by said unit elements is substantially equal to the area of said ultrasonic generating element.

2. The apparatus of claim 1, wherein said unit elements are arranged radially and concentrically with respect to the focus of said ultrasonic generating element.

3. The apparatus of claim 1, wherein each unit element has opposite sides, and includes a ground potential electrode on one side thereof, and a signal electrode on the other side thereof.

4. The apparatus of claim 3, wherein said signal electrode of each said unit element has a surface area smaller than the surface area of the one side.

5. The apparatus of claim 4, wherein each said signal electrode is spaced at least 1 mm from the outer periphery of said unit element.

6. The apparatus of claim 1, wherein each said unit element is individually detachable.

7. The apparatus of claim 1, including means for supporting said plurality of unit elements to form a partially spherically shaped face.

8. An ultrasonic medical treatment apparatus comprising:
- a supporting member;
- a plurality of base plates removably attached to said supporting member; and
- a plurality of unit piezoelectric elements, said elements being adapted to radiate ultrasonic energy at a therapeutic level for patient treatment, said elements being of different shapes with surface areas substantially equal to each other, attached to the base plates.

9. The apparatus of claim 8, wherein said plural unit elements each includes a partially spherically shaped surface.

10. An ultrasonic medical treatment apparatus, comprising:
- a supporting plate having a hole at the center thereof for inserting an ultrasonic probe;
- a plurality of base plates removably attached to said supporting plate, said base plates having fan-shaped surfaces substantially equal in area to each other;
- a plurality of pairs of fan-shaped unit elements having opposite sides, and adhering to the fan-shaped surfaces of said respective base plates pair of the elements of each pair having substantially equal surface areas and different shapes from each other;
- a ground potential electrode provided on the one side of each said unit element; and
- a plurality of signal electrodes provided on the other side of each said unit element.

11. The apparatus of claim 10, further comprising plural electrode-lead passing bores piercing through said supporting plate and said plural base plates attached thereto, and reaching the other sides of said respective unit elements.

* * * * *